(12) United States Patent
Talja et al.

(10) Patent No.: US 6,171,338 B1
(45) Date of Patent: Jan. 9, 2001

(54) BIODEGRADABLE SURGICAL IMPLANTS AND DEVICES

(75) Inventors: Martti Talja, Lahti; Pertti Törmälä, Tampere; Pentti Rokkanen; Seppo Vainionpää, both of Helsinki; Timo Pohjonen, Tampere, all of (FI)

(73) Assignee: Biocon, Oy, Tampere (FI)

( * ) Notice: Under 35 U.S.C. 154(b), the term of this patent shall be extended for 0 days.

(21) Appl. No.: 08/304,082

(22) Filed: Sep. 6, 1994

Related U.S. Application Data

(63) Continuation-in-part of application No. 07/681,529, filed on Jul. 9, 1991, now abandoned.

(30) Foreign Application Priority Data

Nov. 10, 1988 (FI) .......................................................... 885164
Nov. 7, 1989 (WO) ..................................... PCT/FI89/00204

(51) Int. Cl.[7] ....................................................... A61F 2/02
(52) U.S. Cl. ........................................... 623/11.11; 623/1
(58) Field of Search ................................ 623/1, 2, 11, 12, 623/15, 16; 606/151, 152, 153, 154, 157, 158

(56) References Cited

U.S. PATENT DOCUMENTS

| | | | |
|---|---|---|---|
| 4,089,071 | * 5/1978 | Kalnberz et al. ....................... 623/16 |
| 4,366,183 | * 12/1982 | Ghommidh et al. .................. 623/16 |
| 4,595,007 | 6/1986 | Mericle . |
| 4,610,688 | 9/1986 | Silvestrini et al. . |
| 4,652,264 | 3/1987 | Dumican . |
| 4,655,771 | 4/1987 | Wallsten . |
| 4,668,557 | * 5/1987 | Lakes ...................................... 623/1 |
| 4,713,070 | * 12/1987 | Mano ...................................... 623/1 |
| 4,713,076 | * 12/1987 | Draenert ............................... 623/16 |
| 4,743,257 | * 5/1988 | Tormala et al. ....................... 623/16 |
| 4,743,480 | * 5/1988 | Campbell et al. ....................... 623/1 |
| 4,792,336 | 12/1988 | Hlavacek et al. ..................... 623/13 |
| 4,834,755 | 5/1989 | Silvestrini et al. . |
| 4,839,215 | * 6/1989 | Starling et al. ....................... 623/16 |
| 4,863,475 | * 9/1989 | Anderson et al. .................... 623/16 |

(List continued on next page.)

FOREIGN PATENT DOCUMENTS

| | | |
|---|---|---|
| 0121362 | * 10/1984 | (EP) . |
| 0122744 | * 10/1984 | (EP) . |
| 0202444 | * 11/1986 | (EP) . |
| 8303752 | * 11/1983 | (WO) . |
| 8805312 | * 7/1988 | (WO) . |
| WO88/05312 | 7/1988 | (WO) . |
| 8806872 | * 9/1988 | (WO) . |
| WO88/06872 | 9/1988 | (WO) . |

OTHER PUBLICATIONS

Williams, CRC Series in Biocompatibility, Biocompatibility of Clinical Implant Materials (vol. II), 1981, CRC Press, Inc., Boca Raton, Florida, pp. 60–66.

* cited by examiner

Primary Examiner—David Isabella
(74) Attorney, Agent, or Firm—Kenyon & Kenyon

(57) ABSTRACT

A surgical device made of biodegradable material for keeping open a tissue cavity. The tissue includes at least one tissue type selected from the group consisting of healthy tissue or parts thereof, operated tissues or parts thereof, and damaged tissue or parts thereof. The device includes an elongated rod made of the biodegradable material. The elongated rod is at least partially wound, at least once, around a winding center into a helical configuration in a manner that there exists a space free of material of the biodegradable rod between portions of the elongated rod that are adjacent in the wound structure. The rod is at least partially reinforced with biodegradable reinforcement elements oriented in the longitudinal direction of the elongated rod so as to produce an opening force in the winding due to the effect of the winding of the elongated rod into the helical configuration.

14 Claims, 13 Drawing Sheets

U.S. PATENT DOCUMENTS

| | | | |
|---|---|---|---|
| 4,902,508 | * | 2/1990 | Badylak et al. ......................... 623/1 |
| 4,923,470 | * | 5/1990 | Dumican .................................. 623/1 |
| 4,942,875 | * | 7/1990 | Hlavacek et al. ....................... 623/1 |
| 4,956,178 | * | 9/1990 | Badylak et al. ......................... 623/1 |
| 4,990,131 | * | 2/1991 | Dardik et al. ............................ 623/1 |
| 5,024,671 | * | 6/1991 | Tu et al. .................................. 623/1 |
| 5,084,051 | * | 1/1992 | Tormala et al. ........................ 623/16 |
| 5,084,065 | * | 1/1992 | Weldon et al. .......................... 623/1 |
| 5,108,424 | * | 4/1992 | Hoffman, Jr. et al. .................. 623/1 |
| 5,131,907 | * | 7/1992 | Williams et al. ........................ 623/1 |
| 5,131,908 | * | 7/1992 | Dardik et al. ............................ 623/1 |
| 5,147,400 | * | 9/1992 | Kaplan et al. ........................... 623/1 |
| 5,160,341 | * | 11/1992 | Brenneman et al. .................. 623/12 |

TRANSFORMATION OF LAMELLARSTRUCTURE TO FIBRILLAR STRUCTURE

FIBRILS

1μ

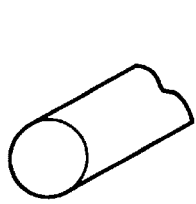
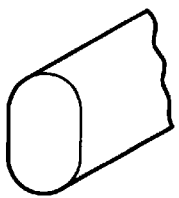
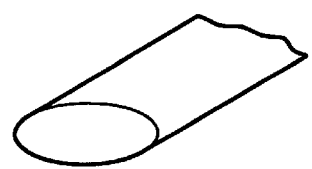
FIG.11a  FIG.11b  FIG.11c
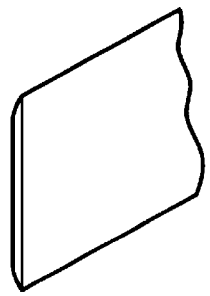
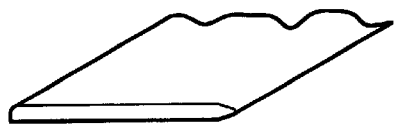
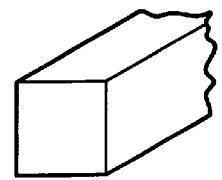
FIG.11d  FIG.11e  FIG.11f
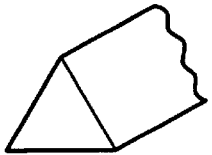
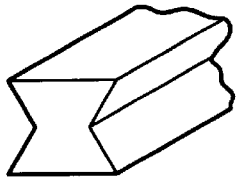
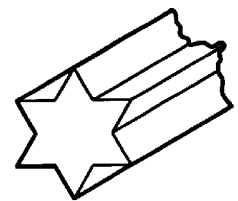
FIG.11g  FIG.11h  FIG.11i
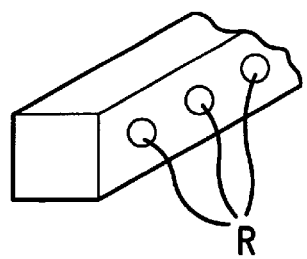
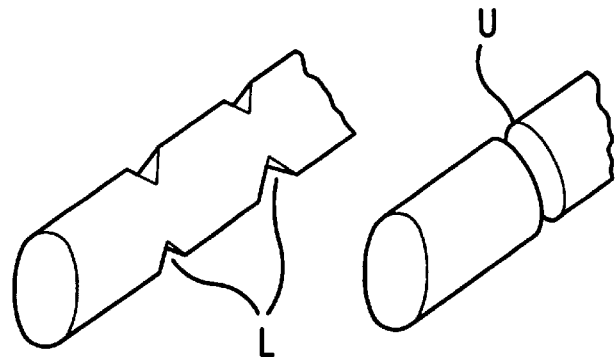
FIG.11j  FIG.11k  FIG.11l

BIODEGRADABLE SURGICAL IMPLANTS AND DEVICES

RELATED APPLICATIONS

This application is a continuation-in-part of U.S. patent application Ser. No. 07/681,529, filed Jul. 9, 1999, now abandoned, the entire disclosure of which are hereby incorporated by reference.

FIELD OF THE INVENTION

The present invention relates to biodegradable surgical implants and/or devices.

BACKGROUND OF THE INVENTION

In surgery, it is known to employ at least partially biodegradable, elongated (typically tubular) surgical implants for supporting, connecting or separating elongated organs, tissues or parts thereof, such as canals, ducts, tubes, intestines, blood vessels, nerves, among others. In this context, a biodegradable, absorbable and/or resorbable, material refers to a material whose decomposition and/or dissolution products leave the system through metabolic ducts, kidneys, lungs, intestines and/or skin by secretion.

Examples of at least partially biodegradable implants include U.S. Pat. No. 3,108,357 to Liebig which suggests a tubular device to be implanted in animals and humans, comprising a resilient woven tube which contains biologically absorbable oxidized cellulose.

Additionally, U.S. Pat. No. 3,155,095 to Brown suggests hollow cylindrical anastomosis joints which are made of an absorbable material.

Further, U.S. Pat. No. 3,272,204 to Artandi and Bechtol suggests collagen-made flexible tubes which can be externally reinforced with a plastic coil or plastic rings.

Other examples of at least partially biodegradable implants include U.S. Pat. No. 3,463,158 to Schmitt and Polistina which suggests fiber-made tubular surgical devices which are at least partially made of absorbable polyglycolic acid (PGA).

U.S. Pat. No. 3,620,218 to Schmitt and Polistina also suggests PGA-made surgical devices, such as tubes.

Still further examples of at least partially biodegradable implants include WO 84/03034 to Barrows which suggests longitudinally openable, porous, coarse-surfaced biodegradable tubes used as a remedy for the nerves.

Additionally, the publication Plast. Rec. Surg. 74 (1984) 329, Dabiel and Olding, suggests an absorbable anastomosis device which comprises cylindrical, tubular, complementary parts.

However, known tubular, at least partially biodegradable surgical implants and devices involve several drawbacks and limitations. As for the implants including biostable parts, such as polymeric, and the like fibers, plastic or metallic coils or rings, or the like, such biostable parts or components remain in a patient's system even after a tissue or an organ has healed. Such components can later be harmful to a patient by causing infections, inflammatory reactions and like foreign matter reactions, and/or they might release particles, corrosion products, or the like which can wander in the system and/or cause harmful cellular level reactions.

Known tubular biodegradable implants manufactured by melt working technique or a like method are often massive and stiff and create, in resilient tissues, such as ducts, tubes, blood vessels, among others, an undesirable stiff, non-physiological bracing effect which can lead to harmful alterations in the properties of a tissue braced. In addition, the massive, tubular implants create a heavy local foreign matter loading the system at the installation site thereof and such loading can also contribute to harmful alterations in an operated tissue, such as canal, tube, duct, blood vessel, or the like.

On the other hand, the tubular structures constructed from biodegradable fibers by braiding, knitting, weaving or some other similar technique do not posses the structural rigidity and/or resilience often required of a support implant to be fitted inside or outside a tubular tissue.

SUMMARY OF THE INVENTION

It has been surprisingly discovered in the present invention that the deficiencies and drawbacks of known, at least partially biodegradable surgical implants and devices used for supporting, connecting or separating organs, tissues or parts thereof can be substantially eliminated with an implant, device or part thereof which is mainly characterized by comprising an at least partially biodegradable elongated member which is at least partially wound at least once around a center of rotation into a helical configuration and which is at least partially reinforced with biodegradable reinforcing elements.

An implant, device or part thereof (hereinbelow "device") according to the present invention can be conceived, having been formed in a manner that around a certain center point is wound some elongated member at a distance of a certain winding radius from the center point. If the winding center is stationary and the winding radius increases as the winding angle increases, the configuration of an obtained device is a spiral configuration, especially if the winding radius remains in the same plane. Provided that the winding radius is constant and the winding center travels during the turning of an elongated member along a certain, for example, linear path, the device obtained has a circle-cylindrical screw-threaded configuration, or helix. On the other hand, if the winding radius changes while the winding center travels along a certain path, there will be produced a spiral configuration whose external surface is in conical shape. It is obvious that the implant, device or part thereof can include the above shapes and configurations as a combination and, for example, a combination of a spiral and a cylindrical screw-threaded configuration. The implant, device or part thereof can also be provided with members of other shapes in addition to a screw-threaded configuration, such as, for example, plates or sleeves.

The present invention relates also to a method for manufacturing an implant, device or part thereof ("device") including at least partially winding at least once an elongated blank formed by a biodegradable polymer matrix and biodegradable reinforcement elements.

The invention relates also to the use of an implant, a device and part thereof.

BRIEF DESCRIPTION OF THE DRAWINGS

The present invention is described in more detail in the following specification with reference made to the accompanying drawings. In the drawings.

FIGS. 11a–11l represent preferred cross sectional shapes and surface patterns for an elongated member, or blank, of embodiments of devices according to the present invention shown in FIGS. 5–10;

Detailed DESCRIPTION OF PREFERRED EMBODIMENTS

In the context of the present invention, the biodegradable reinforcing elements refer to the following:

a) oriented or aligned structural units included in the micro-structure or molecular structure of a material such as oriented parts of molecules or parts thereof or microfibrils, fibrils or the like oriented structural units formed thereby;

b) biodegradable organic filaments, fibers, membrane fibers or the like, or structures constructed thereof, such as bands, braids, yarns, fabrics, non-woven structures or the like; or c) biodegradable inorganic (ceramic) filaments, fibers, membrane fibers or the like, or structures constructed thereof.

A particularly preferred embodiment of the present invention is such an implant or device which is structurally self-reinforced. A self-reinforced biodegradable structure is defined in U.S. Pat. No. 4,743,257 to Törmälä et al. In a self-reinforced structure, a biodegradable polymer matrix is reinforced with biodegradable reinforcement elements or units having the same proportional elemental composition as the matrix. The reinforcement elements are typically oriented molecules or parts thereof or the like obtained by orientation of fibrils, microfibril, fibers, filaments or the like structures constructed thereof.

Reinforcement elements inside the microstructure of a self-reinforced polymer material are produced, for example, by orienting the molecular structure of a material either in melt state or in solid state. In such conditions, the structure-reinforcing orientation remains at least partially, permanently in material either as a result of the rapid cooling and/or solid state of the melt and/or as a result of the prevention of molecular movements (relaxation) of the melt. The self-reinforcement based on draw orientation is described in the invention PCT/FI87/00177, Törmälä et al., as follows.

A partially crystalline, non-oriented piece of polymer typically consists of crystal units, that is, spherolites and amorphous areas thereinside and/or therebetween.

The orientation and fibrillation of a polymer system possessing a spherolitic crystalline structure is a process that has been extensively studied in connection with the production of thermoplastic fibers. For example, U.S. Pat. No. 3,161,709 suggests a three-step drawing process for transforming a melt-worked polypropene filament into a fiber having a high tensile strength.

Figure 19:
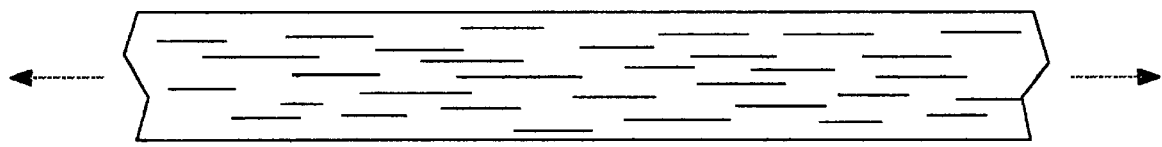
FIG. 19 represents a cross-sectional view of an implant according to an embodiment of the present invention as it is being drawn.

The mechanism of orientation and fibrillation is basically as follows (C. L. Choy et al. Polym. Eng. 30 Sci. 23, 1983, p. 910). As a partially crystalline polymer is being drawn, the molecular chains of crystal lamellae quickly begin to parallel, or orient, themselves in the drawing direction. In other words, the reinforcement elements lie substantially parallel to the longitudinal axis of the rod. The drawing orients the reinforcement elements to the longitudinal direction of the rod. The first phase of the drawing of an implant according to an embodiment of the present invention is illustrated in FIG. 19. As can be seen in FIG. 19, the fibers of the matrix are oriented in the longitudinal direction of the device, the same direction as the drawing, which is indicated by the arrows.

Simultaneously, the spherolites extend in length and finally break. Crystal blocks detach from lamellae and join together as queues by means of tight tie-molecules which are formed through the partial release of polymer chains from crystal lamellae. The alternating amorphous and crystalline zones, together with tight tie-molecules, form long, thin approximately 100 Å wide microfibril which are paralleled in the drawing direction. Since the intrafibrillar tie-molecules form in the phase boundaries between crystal blocks, they will be mainly located on the external surface of microfibrils. Those tie-molecules, which link various lamellae in an isotropic material prior to the drawing, serve in a fibrillated material to link various microfibrils together, that is, become interfibrillar tie-molecules which are located in boundary layers between adjacent microfibrils.

Figure 20:
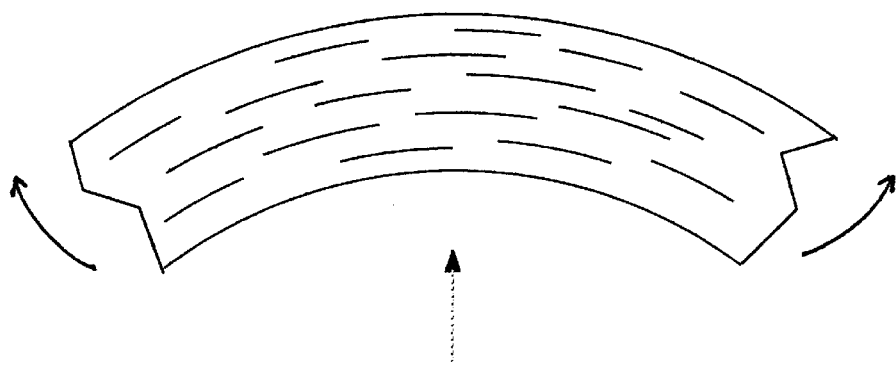
FIG. 20 represents a cross-sectional view of the implant shown in FIG. 19 after being bent.

The rod is then bent by winding to a helical configuration. The bending actually creates a "pre-stress" condition to the wound rod which then tends to open the helix beyond the diameter it was wound. FIG. 20 illustrates the bending and the forces on the implant. The arrows to the right and left of the implant indicate the direction the implant tends to move in response to the bending. In other words, the arrows represent an opening force.

Figure 1:
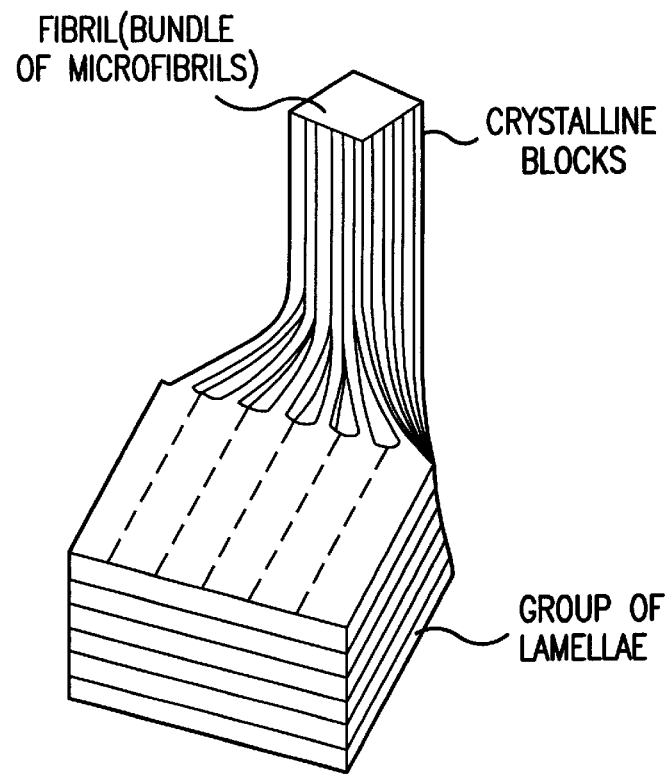
FIG. 1 represents a schematic perspective view of the formation of an array of lamellae turning into a fibrillated structure of a material micro-structure in an embodiment of a device of the invention.
Figure 2:
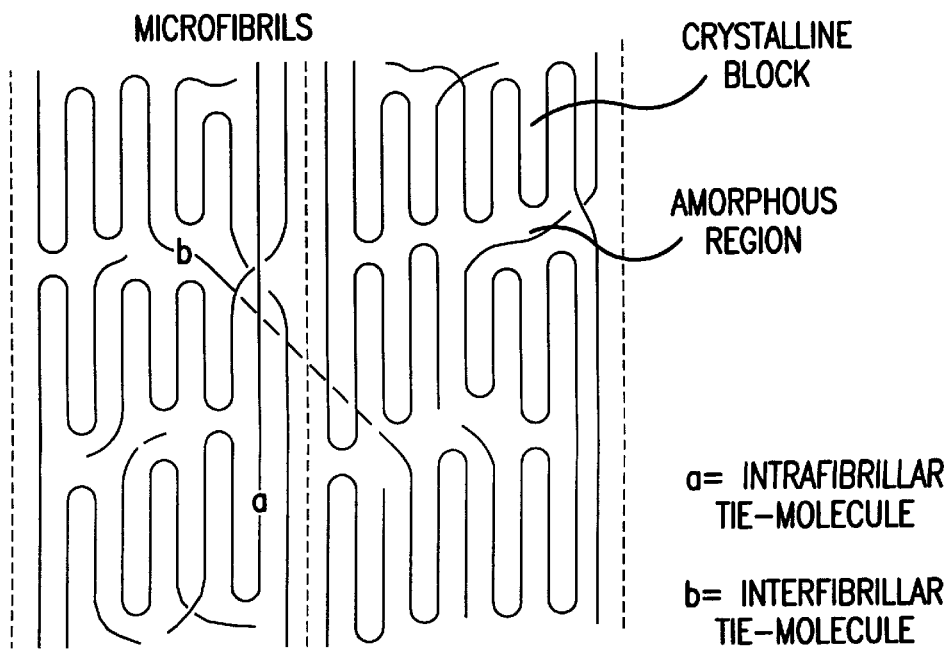
FIG. 2 represents an intra- and inter-fibrillary molecular structure.
Figure 3:
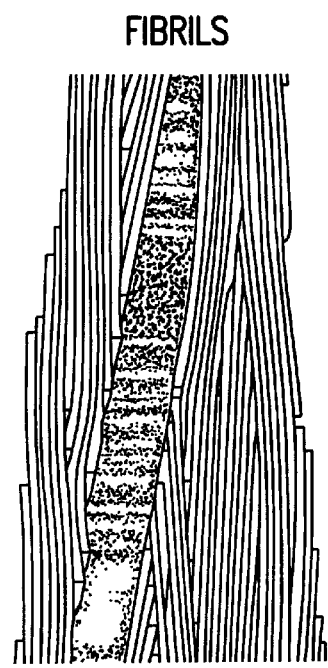
FIG. 3 represents a schematic view of the micro-structure of a fibrillated polymer.

FIG. 1 illustrates, schematically, the transformation of an array of lamellae into a fibrillar structure (a fibril consisting of a bunch of microfibrils) due to the action of water. FIG. 2 shows some of the molecular structure inside and between microfibrils. FIG. 3 illustrates, schematically, some of the structure of a fibrillated polymer. The Figure shows several fibrils one being dyed grey for the sake of clarity, which comprise a plurality of microfibrils having a length of several microns.

Orientation is initiated right at the start of drawing and also a fibrillated structure is formed at rather low drawing ratios $\lambda$, wherein $\lambda$=(length of a piece after drawing)/(length of piece prior to drawing). For example, HD-polyethene is clearly fibrillated at $\lambda$ value 8 and polyacetal (POM) at $\lambda$ value 3.

As the drawing of a fibrillated structure is continued further (this stage of the process is after referred to as ultra-orientation), the structure is further deformed with microfibrils sliding relative to each other to further increase the proportional volume of straightened interfibrillar tie-molecules. If the drawing is effected at a sufficiently high temperature, the oriented tie-molecules crystallize and build axial crystalline bridges which link together crystalline blocks.

The excellent strength and modulus of elasticity properties of a fibrillated structure are based on the vigorous orientation of polymer molecules and polymer segments in the direction of drawing (in the direction of the longitudinal axis of microfibrils) characteristic of the structure.

The fibrillation of macroscopic polymeric blanks, such as rods or tubes, is prior known in the cases of biostable polyacetal and polyethene (See K. Nakagawa and T. Konaka, Polymer 27, 1986, p. 1553 and references included therein). What has not been prior known, however, is the orientation and fibrillation of at least partially helical and/or spiral or similarly shaped members or pieces manufactured from biodegradable polymers.

The at least partial orientation and/or fibrillation of a biodegradable helical and/or spiral or similar piece can be effected, for example, by rapidly chilling a flowing state polymer melt, for example, in an injection mold, into a solid state in a manner that the orientation of molecules existing in the flowing melt in flowing direction is not allowed to discharge through molecular movements either entirely or partially into a state of random orientation.

A more vigorous orientation and fibrillation and, thus, also improved mechanical qualities are generally provided for a polymer piece by mechanically working the material (orientation), and generally drawing or hydrostatic extrusion or die-drawing in such a physical condition (usually in solid state). Under these conditions, it is possible for the material to undergo dramatic structural deformations in its crystalline structures and amorphous areas occurring at the molecular level for creating orientation and fibrillation. As a result of fibrillation, for example, a restorable polymer material produced by injection molding or extrusion and initially possessing mainly a spherolitic crystalline structure, transforms into a fibrillated structure which is vigorously oriented in the direction of drawing and comprises, for example, elongated crystalline microfibrils as well as tie-molecules linking them as well as oriented amorphous areas. In a partially fibrillated structure, the amorphous areas between microfibrils make up a more substantial portion of the material than in an ultra-oriented material which, in most preferred case, only includes amorphousness as crystal defects. As a result of orientation, fibrillation and ultra-orientation, the values of strength and modulus of elasticity of a material are multiplied compared to a non-fibrillated structure.

Orientation and the resulting fibrillation can be used for treating biodegradable polymers, copolymers and polymer compositions so as to form self-reinforced composites in which nearly the entire material stock is oriented in a desired fashion and the portion of amorphous matrix is small. The stock orientation and small amount of matrix result in such materials having extremely high quality strength properties in orientation direction with a bending strength, for example, up to 400–1500 MPa and modulus of elasticity 20–50 GPa. Thus, the orientation and fibrillation can be used to provide helixes or spirals or the like devices with multiple strength values compared to those of normal melt-processed biodegradable materials, which are typically in the order of 30–80 MPa.

Figure 4:
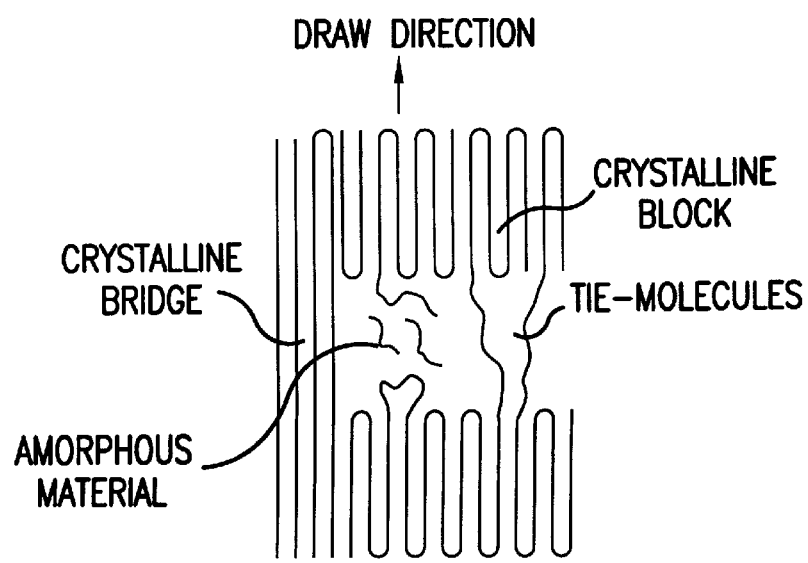
FIG. 4 represents a schematic view of the molecular structure of fibrillated devices according to embodiments of the present invention.

As in the fibrillated structure of polymer fibers, in the structure of fibrillated devices, there can be found, for example, the following structural units, which are schematically shown in FIG. 4: crystalline blocks, the stock therebetween comprising an amorphous material, for example, loose polymer chains, chain ends and molecular folds; tie-molecules which link the crystalline blocks together, the number and tightness of these increases as drawing ratio $\lambda$ increases; as well as possible crystalline bridges between crystalline blocks. Bridges can form during the drawing as tie-molecules orient and group themselves as bridges (C. L. Choy et al., J. Polym. Sci., Polym. Phys. Ed., 19, 1981, p. 335).

The oriented fibrillated structure shown in FIGS. 1–4 is already developed by using so-called "natural" drawing ratios 3-8. As drawing is then continued as ultra-orientation, the portion of crystalline bridges can increase to be quite considerable whereby, in the extreme case, the bridges and crystal blocks provide a continuous crystalline structure. However, the effects of tie-molecules and bridges are often similar and, thus, the exact distinction thereof from each other is not always possible.

Orientation and fibrillation can be experimentally characterized by the application of several different methods. Orientation function (fc), which can be determined by X-ray diffraction measurements, characterizes orientation of the molecular chains of a crystalline phase. Generally, fc already reaches a maximum value of 1 by natural drawing ratios ($\lambda$<6). For polymer materials having a spherolitic structure fc<<1.

Double-refraction ($\Delta$) measured with a polarization microscope is also a quantity which represents the orientation of molecular chains. It generally increases at natural drawing ratios ($\lambda$<6) vigorously and, thereafter, in ultra-orientation more slowly, which indicates that the molecular chains of a crystalline phase orient vigorously in the drawing direction at natural drawing ratios and orientation of the molecules of an amorphous phase continues further at higher drawing ratios (C. L. Choy et al., Polym Eng. Sci., 23, 1983, p. 910).

The formation of a fibrinous structure can also be demonstrated visually by studying the fibrillated material by means of optical and/or electrical microscopy (see e.g. T. Knoda et al., Polymer, 26, 1985, p. 462). Even the individual fibrils consisting of microfibrils can be clearly distinguished in scanning electron microscope images of a fibrillated structure.

An oriented and/or fibrillated and/or ultra-oriented piece (blank) is then rotated at least once around a center of rotation into helical configuration to form "a device" of the invention by shaping the blank at least partially by means of an external force or pressure and/or external heat and/or by means of heat inducible in the piece, for example, by radiowave radiation. In practice, the rotation of winding of the device is effected in a manner that an elongated blank is wound around a suitable, if necessary heated mold, for example, a mold of cylindrical shape). Such a mold is typically round in cross-section so as to produce helical shapes having a circular cross-section. The cross-sectional shape of a mold can also be, for example, elliptical, oval, or angular to produce helical shapes having various cross-sections. Orientation, fibrillation or ultra-orientation can also be effected in a continuous action and/or simultaneously with winding in a manner that an elongated blank is being drawn and the drawn section is simultaneously wound around a cylindrical mold.

At least partially oriented and/or fibrillated and, particularly, ultra-oriented biodegradable devices are an example of an oriented, self-reinforced biodegradable (U.S. Pat. No. 4,743,257, Törmälä et al.) composite material, wherein the oriented reinforcement elements, such as fibrils, microfibrils, crystal blocks, tie-molecules or crystallized bridges, among others, are formed and/or grouped during a mechanical working and a phase binding. The oriented reinforcement elements comprise, for example, of the following structural elements: amorphous phase, interfaces between crystal blocks as well as interfaces between bridges and microfibrils, a typical feature of which is also a vigorous orientation in a drawing direction.

Another method for using biodegradable reinforcement elements in devices of the invention is the reinforcement thereof with fibers manufactured from polymer, copolymer or a polymer composition, with film fibers, filaments or structures constructed thereof, such as braids, threads, ribbons, non-woven structures, fabrics, knittings or the like, by combining readymade fibers with a suitable polymer matrix. Such fibers can be manufactured, for example, from biodegradable polymers set forth in Table 1. The fibers can also be biodegradable ceramic fibers, such as calcium phosphate fibers (see e.g. S. Vainionpää et al., Progr. Polym. Sci., in printing).

Various plastic technological methods can be applied to manufacture devices of the present invention reinforced with biodegradable organic and/or inorganic fibers or with structures constructed thereof. The manufacturing may be carried out by binding the reinforcement structures at least partially to each other with biodegradable polymer, copolymer or a polymer composition (matrix) in such conditions which serve to produce a sufficiently equal quality composite from the matrix and reinforcement elements. The matrix is usually in solution or melt state. Methods for combining reinforcement fibers or the like and a matrix as well as for processing them into semi-finished products and/or devices include, among others, injection molding, extrusion, pultrusion, winding, and compression molding.

An at least partially spirally shaped, at least partially biodegradable device according to the present invention can be used in a versatile manner for supporting, expanding, joining or separating organs, tissues or parts thereof. A device according to the present invention offers a plurality of benefits over the prior art implants and devices. When using a device according to the invention, the amount of foreign matter remains smaller than with traditional implant tubes. Devices according to the present invention are more flexible and resilient than the rigid prior art tubes and, on the other hand, devices according to the present invention are stronger under compression and retain their shape better that fiber-constructed tubular devices, whereby devices according to the present invention are capable of being used for retaining open or even expanding the medullary cavity of tubular tissues.

Devices of the present invention can be manufactured from biodegradable polymers, copolymers and polymer compositions. Table 1 shows a number of prior known biodegradable polymers, which or mixtures of which can be used as raw material for devices of the present invention both as a matrix (or binder polymers) and/or reinforcement elements.

TABLE 1

| Biodegradable polymers |
| --- |
| 1. Polyglycolide (PGA) <br>    Copolymers of glycolide |
| 2. Glycolide/lactide copolymers (PGA/PLA) |
| 3. Glycolide/trimethylene carbonate copolymers (PGA/TMC) <br>    Polylactides (PLA) <br>    Stereoisomers and copolymers of PLA |
| 4. Poly-L-lactide (PLLA) |
| 5. Poly-D-lactide (PDLA) |
| 6. Poly-DL-lactide (PDLLA) |
| 7. L-lactide/DL-lactide copolymers <br>    L-lactide/D-lactide copolymers <br>    Copolymers of PLA |
| 8. Lactide/tetramethylene glycolide copolymers |
| 9. Lactide/trimethylene carbonate copolymers |
| 10. Lactide/δ-valerolactone copolymers |
| 11. Lactide/ε-caprolactone copolymers |
| 12. Polydepsipeptides (glycine-DL-lactide copolymer) |
| 13. PLA/ethylene oxide copolymers |
| 14. Asymmetrically 3,6-substituted poly-1,4-dioxane-2,5-diones |
| 15. Poly-β-hydroxybutyrate (PHBA) |
| 16. PHBA/β-hydroxyvalerate copolymers (PHBA/PHVA) |
| 17. Poly-β-hydroxypropionate (PHPA) |
| 18. Poly-β-dioxanone (PDS) |
| 19. Poly-δ-valerolactone |
| 20. Poly-ε-caprolactone |
| 21. Methylmethacrylate-N-vinylpyrrolidone copolymers |
| 22. Polyesteramides |
| 23. Polyesters of oxalic acid |
| 24. Polydihydropyranes |
| 25. Polyalkyl-2-cyanoacrylates |
| 26. Polyuretanes (PU) |
| 27. Polyvinyl alcohol (PVA) |
| 28. Polypeptides |
| 29. Poly-β-maleic acid (PMLA) |
| 30. Poly-β-alkanoic acids |
| 31. Polyethylene oxide (PEO) |
| 32. Chitin polymers |

Reference: S. Vainionpää, P. Rokkanen and P. Törmälä, Progr. Polym. Sci., in printing It is obvious that biodegradable polymers other than those set forth in Table 1 can also be used as raw materials for implants, devices or parts thereof. For example, the biodegradable, absorbable polymers described in the following publications can be used for the above purposes: U.S. Pat. No. 4,700,704 to Jamiolkows and Shalaby; U.S. Pat. No. 4,655,497 to Bezwada, Shalaby and Newman; U.S. Pat. No. 4,649,921 to Koelmel, Jamiolkows and Bezewada; U.S. Pat. No. 4,559,945 to Koelmel and Shalaby; U.S. Pat. No. 4,532,928 to Rezada, Shalaby and Jamiolkows; U.S. Pat. No. 4,605,730 to Shalaby and Jamiolkows; U.S. Pat. No. 4,441,496 to Shalaby and Koelmel; U.S. Pat. No. 4,435,590 to Shalaby and Jamiolkows; and U.S. Pat. No. 4,559,945 to Koelmel and Shalaby.

It is also natural that devices of the present invention may contain various additives and adjuvants for facilitating the processability of the material such as, for example, stabilizers, antioxidants or plasticizers; for modifying the properties thereof such as, for example, plasticizers or powdered ceramic materials or biostable fibers such as, for example, carbon fibers; or for facilitating the manipulation thereof such as, for example, colorants.

According to one preferred embodiment, devices of the present invention may contain some bioactive agent or agents, such as antibiotics, chemotherapeutic agents, wound-healing agents, growth hormone, contraceptive agent, anticoagulant, such as heparin. Such bioactive devices are particularly preferred in clinical applications since, in addition to mechanical effect, they have biochemical, medical and the like effects in various tissues.

Devices of the present invention can also be advantageously combined with other types of biodegradable implants and devices. For example, by inserting a helical device as shown in FIGS. 7–10 into a tube woven or knitted from biodegradable and/or biostable thread there is obtained a firm and resilient tube which has a variety of applications in surgery for replacing or supporting tissues and/or for keeping open the cavities within or between tissues.

A device according to the present invention can also be fitted with long biodegradable rods which extend parallel to the longitudinal axis of, for example, a helically-shaped device. Thus, if necessary, the device can be braced to form a tubular structure.

A device according to the invention can also be fitted with various other accessories, such as flat, perforated plates at the ends of a device for securing the ends of a device firmly to the surrounding tissues by means of surgical stitches.

Figure 5:
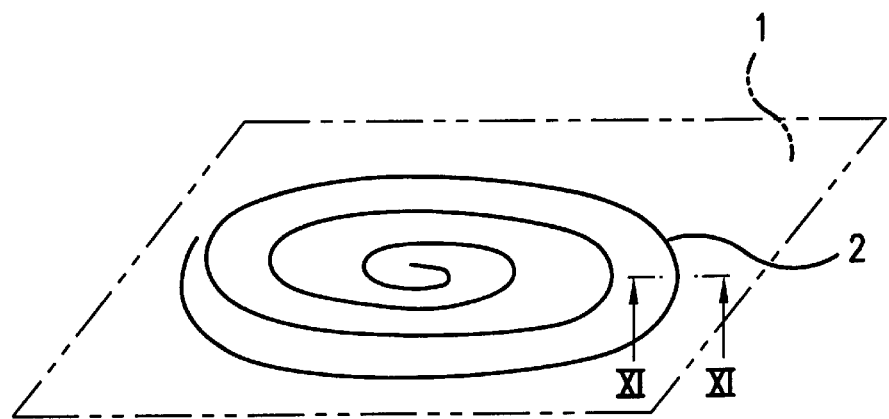
FIGS. 5 and 6 represent schematic perspective views of spiral-shaped embodiments of an embodiment of a device according to the present invention.
Figure 6:
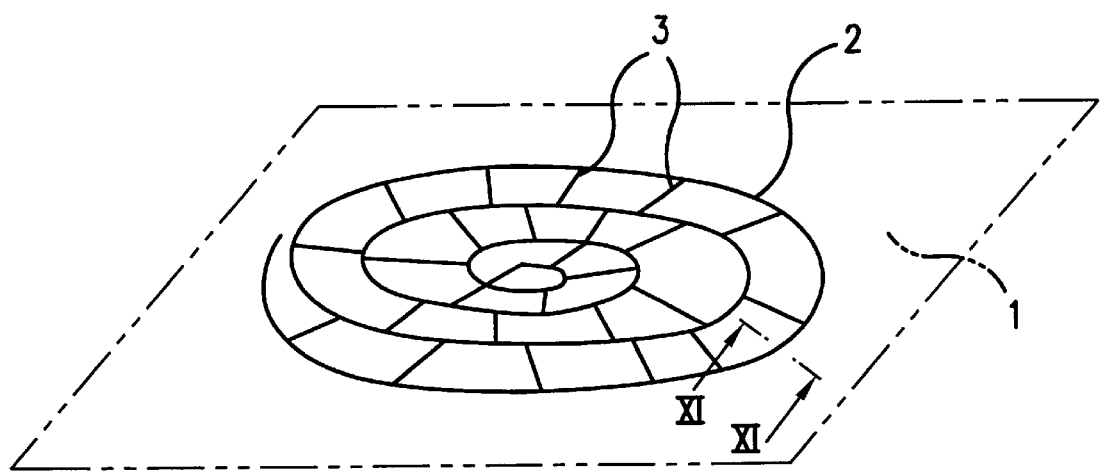

Devices according to the present invention can have various geometrical configurations. For example, FIG. 5 illustrates a flat or planar (in imaginary plane 1) spiral 2 that can be used as a resilient separating material between tissues. The helixes of spiral 2 can also be connected with each other by means of biodegradable radial wires, rods 3 or the like as shown in FIG. 6. The spiral has a high strength in the direction of plane 1 but is resilient in the direction perpendicular to that plane.

A device according to the present invention can also vary in its dimensions in various sections thereof. For example, FIGS. 7a–10a and 7b–10b schematically illustrate a few such devices. These devices may be used for providing external and/or internal support for organs or their parts of various shapes such as liver, spleen, kidneys, intestines, among others.

Figure 7A:
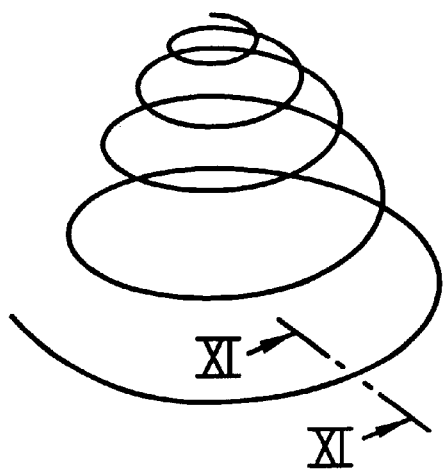
FIGS. 7a–9b represent schematic perspective views of conical embodiments of devices according to the present invention.
Figure 8A:
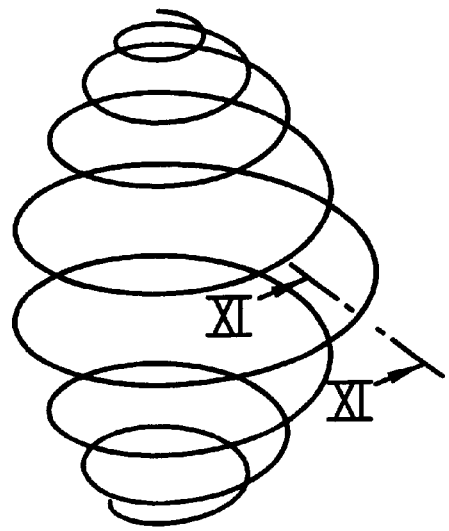
Figure 9A:
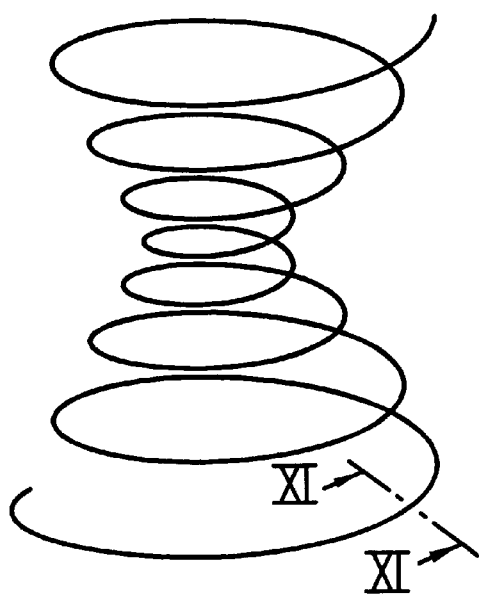
Figure 7B:
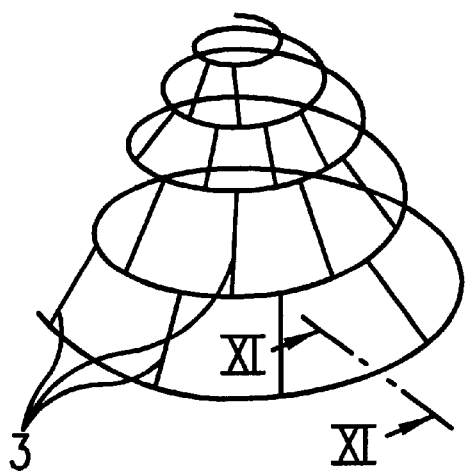
Figure 8B:
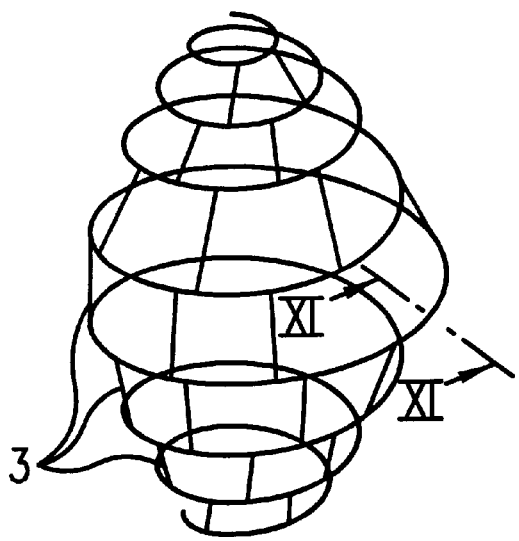
Figure 9B:
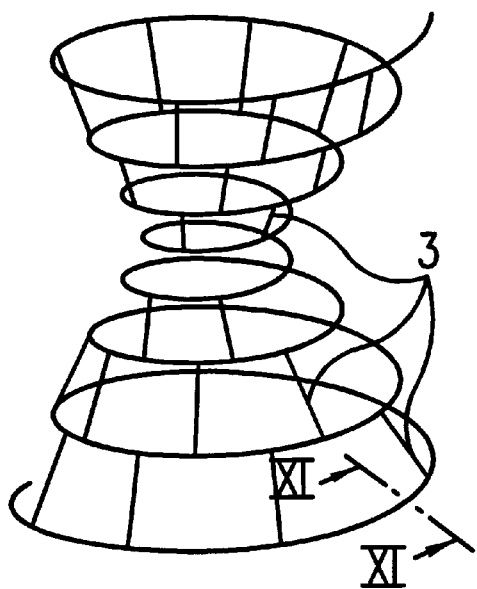

A device shown in FIG. 7a is wound into a conical body. The conical body can have a side face outline which is either straight or arched or a combination thereof according to the intended application. Devices shown in FIGS. 8a and 9a include two conical bodies joined to each other either at the base of conical bodies as shown in FIG. 8a, or at the apex thereof, as shown in FIG. 9a. FIG. 10 illustrates a device having its outer face wound into a cylindrical configuration.

FIGS. 7b, 8b, 9b and 10b illustrate device configurations matching those of FIGS. 7a, 8a, 9a and 10a and fitted rods 3 connecting the turns of helical body.

Figure 10A:
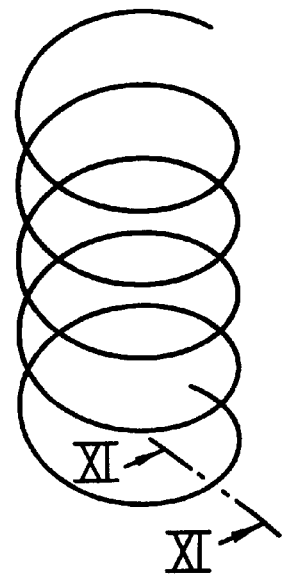
FIGS. 10a and 10b represent schematic perspective views of a cylindrical embodiment of a device according to the present invention.
Figure 10B:
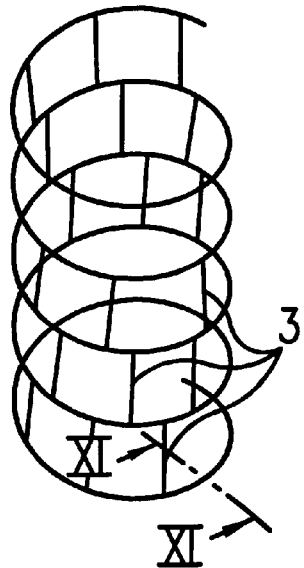
Figure 10D:
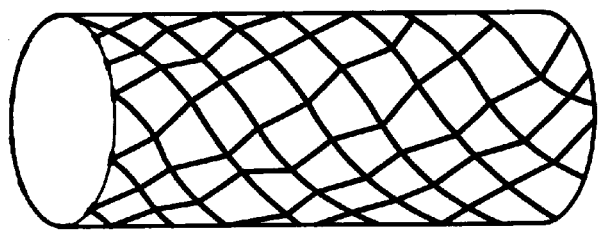
FIGS. 10c and 10d represent further embodiments of a cylindrical device according to the present invention.
Figure 10C:
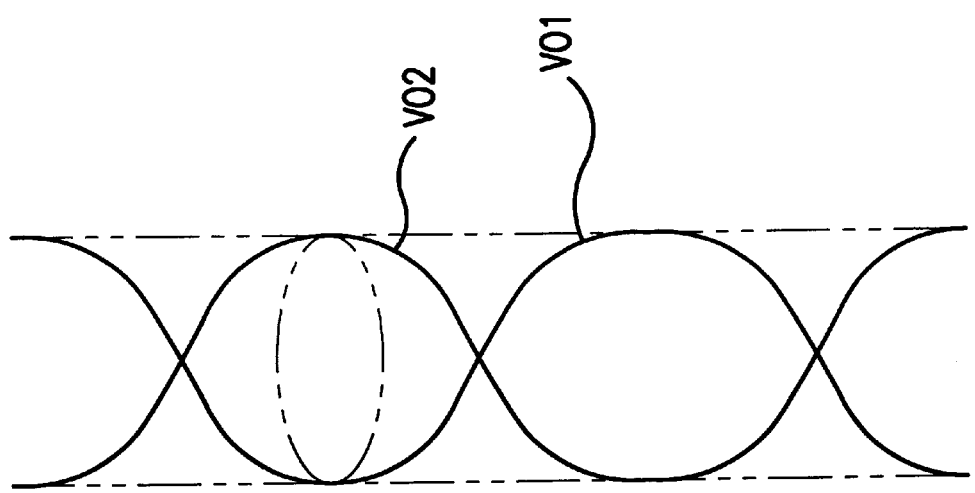

Furthermore, FIG. 10c shows an embodiment in which the device is comprised of two nested device elements VO1 and VO2 wound into a helical configuration preferably in opposite directions. Each has a cylindrical helical configuration. FIG. 10d shows an embodiment of a device, wherein a number of device elements wound into a helical configuration have been twined together. The device elements are adapted to run alternately over and under each other to form a tubular structure.

FIGS. 11a–11l illustrate some types of cross-sections for a blank. A blank for manufacturing devices of the present invention can have a cross-section which is, for example, circular (11a), elliptical (11b, 11c), flat (11d, 11e), angular (11f, 11g, 11h) or asteroid (11i). By varying the cross-section of a blank it is possible to effect, for example, on the mechanical properties of a device, the growth of tissues on the surface of a blank and the growth of tissues through the device. The thickness of a blank can also vary in different sections of a blank or it can be provided with holes R (11j) or similar structures, such as recesses L (11k) or slots (11l) for facilitating the fastening or securing thereof to tissues.

Figure 12A:
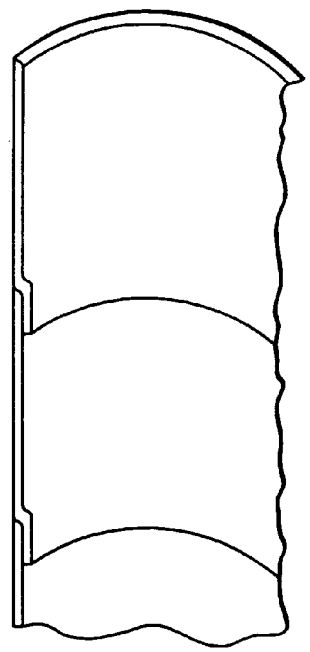
FIGS. 12 and 13 represent a schematic perspective view of an embodiment of the invention.
Figure 12B:
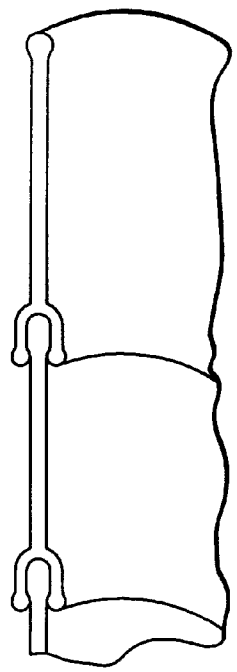
Figure 13A:
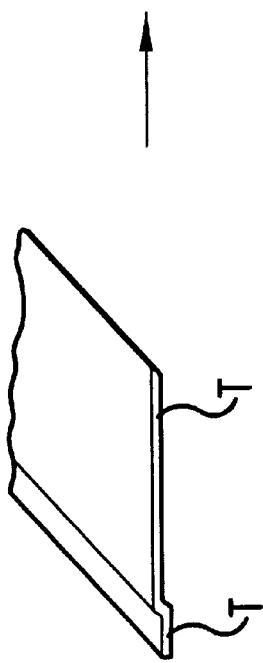
Figure 13B:
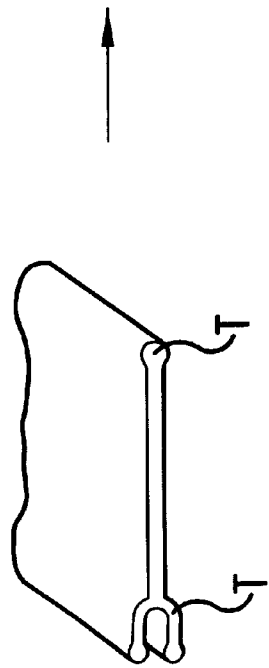

According to one preferred embodiment, a device of the present invention is manufactured by winding or rolling a flat blank having a cross-section shown in FIG. 12 into a tube as shown in FIG. 13. Since the longitudinal edges of a blank as shown in FIGS. 12a and 13a are provided with folded or other gripping means T which engage each other, during the winding, there will be formed a flexible tube that can be used in the treatment of, for example, a windpipe or the like flexible tissue channels as a temporary prothesis.

Figure 18A:
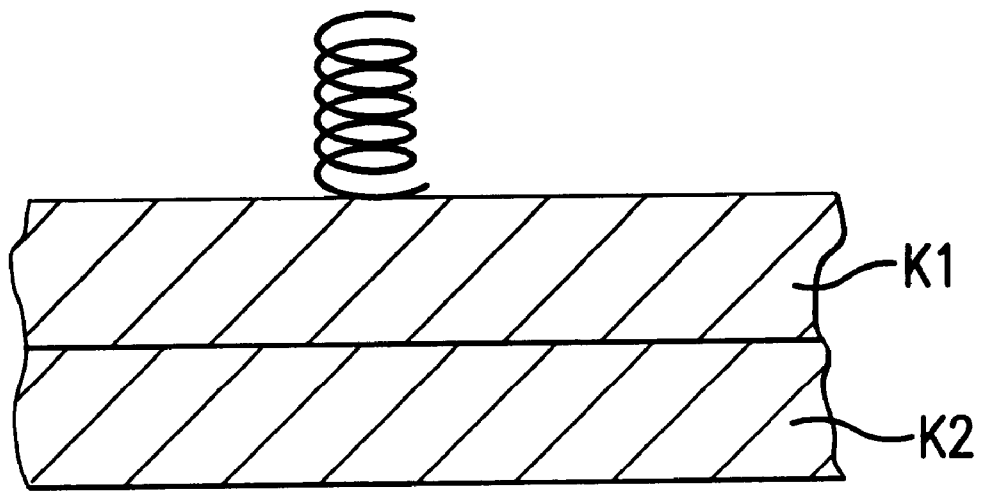
FIG. 18 represents another embodiment of a device according to the present invention.
Figure 18B:
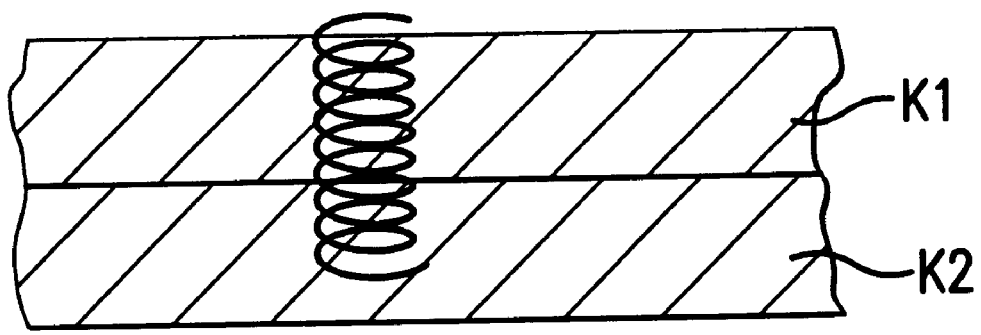

According to one preferred embodiment, devices of the present invention can be used to join together tissues, organs or parts thereof, such as muscular tissue or the other soft tissues. Such an embodiment is illustrated in FIG. 18. FIG. 18a shows a cross-section of a tissue K1 and a tissue K2 which should be joined with each other. The joining can be effected by using a sharp-pointed spiral S which is driven in the same way as a corkscrew through the tissues (FIG. 18b). By locking the top portion of a spiral in position after the turning, for example, by stitching the spiral firmly to surrounding tissues by means of surgical stitches dissolving through the holes made in the spiral blank, the spiral serves to secure tissues K1 and K2 to each other preventing the separation or sliding thereof relative to each other.

Unexpectedly, embodiments of the present invention will expand upon implantation into tissue. The expansion may, therefore, provide the surprising advantage of helping to lock the implant in place. This expansion is the result, at least in part, of the composition and manufacturing technique of the invention and of the reaction of the invention to the body temperatures to which the invention may be subjected to after implantation. The expansion of the implant may be at least about 15% when it is implanted in conditions of living tissue.

The present invention and its applicability is described in more detail by means of the following examples.

EXAMPLE 1

Some polymers set forth in Table 1 were used to prepare helical devices of the present invention. An example, such as that shown in FIG. 10, includes blank thickness 1 mm, outer diameter of helix 6 mm, inner diameter 4 mm, pitch angle 15 degrees and length of device 15–20 mm. The polymeric melt is subjected to injection molding to produce blanks having a diameter ($\phi$) of 1.5–2.0 mm by drawing (orientation and self-reinforcement) then at a temperature of TM>T>Tg, wherein Tg is polymer glazing temperature and Tm is polymer (possibly) melting temperature, to the $\phi$ reading of 1 mm and by winding them in hot state around a metal pipe of diameter 4 mm. The device is then cooled and the finished device is removed from the surface of the metal pipe.

Figure 14A:
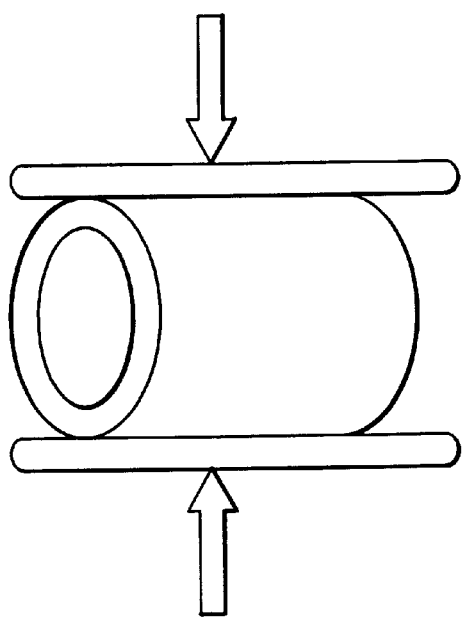
FIG. 14 represents a schematic view of an embodiment of a test arrangement according to the present invention described in example 1.
Figure 14B:
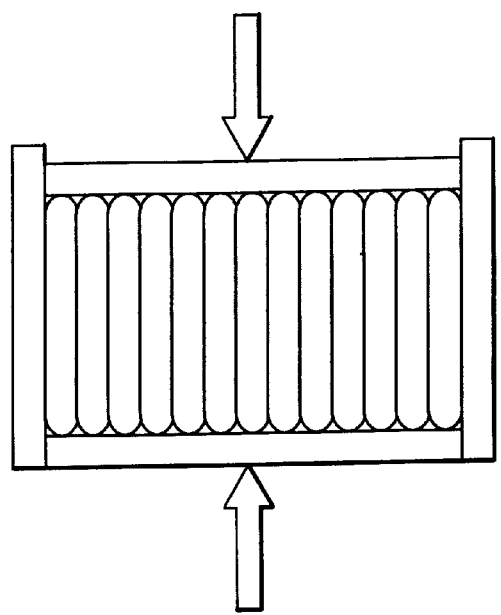

Reference materials were made by using similar polymers to prepare tubular pieces including a tube length of 10 mm, outer diameter of 6 mm and inner diameter of 4 mm by injection molding polymer melt into cooled tubular mold. The compression strength of the devices and that of the corresponding tubes were compared to each other by squeezing a device (FIG. 14b) or a tube (FIG. 14a) placed between two steel plates with an external force in the direction orthogonal to its longitudinal axis. The bending of a device in lateral direction was prevented by prepressing the device into a compact bundle between two vertical plates (FIG. 14b).

The compression load strengths of a tube (FIG. 14a) a device (FIG. 14b) made of the same polymer and having equal weights were compared to each other. This was followed by the determination of the relative compression load strength (SP) of the device using the formula: (force required to fracture the device)/(force required to fracture the tube). Devices and tubes were manufactured by using the following biodegradable polymers, copolymers and polymer compositions: polyglycolide (Mw 60,000), glycolide/lactide copolymer (Mw 40,000), glycolide/trimethylenecarbonate copolymer (Mw 60,000), PLLA (Mw 260,000), PDLLA (Mw 100,000), lactide/δ-valerolactone copolymer (Mw 60,000), lactide/ε-capro-lactone copolymer (Mw 60,000), PHBA (Mw 700,000), PHPA (Mw 50,000) and PDS (Mw 40,000). Resulting values for SP were ranging between 1.8–12.

EXAMPLE 2

Devices of the invention such as that shown in FIG. 10 were prepared by using a biodegradable polymer matrix as well as biodegradable reinforcing fibers included therein as reinforcements. A bundle of parallel fibers and fine particulate thermoplastic polymer powder of particle size 1–10 μm mixed therein were compression molded in a rod-shaped mold of length 8 cm, φ1.5 mm above the melting point for partially crystalline polymers, or glazing point, for amorphous polymers of the matrix polymer. The amount of reinforcing fibers was 40–60% by volume. The rod blanks were helically wound in a heated condition around a hot cylindrical mold with an outer diameter of helix 8 mm and the mold was cooled. When using an n-butylcyano acrylate reaction polymer as a matrix, the bundle of reinforcing fibers was rapidly impregnated with cyanoacrylate and the uncured wetted bundle of threads was wound helically around a teflon-coated steel pipe followed by wetting and removing the device. A corresponding device was made by using just cyanoacrylate.

Impregnation technique was also applied when using a matrix containing segmented polyurethane (S. Gogolewski and A. Pennings, Makromol. Chem. Rapid Comm. 4, 1983, p. 213) which was dissolved in N,N"-dimethylformamide/tetrahydrofurane solution, weight ratio 3/2. Then, the bundle of fibers, helically wound on the surface of a teflon-coated pipe, was impregnated at 80 degrees with a polyurethane solution and the pipe was immersed in a mixture of ethanol/distilled water (1:1). This process was repeated several times for preparing the device. A corresponding device was made by using just polyurethane.

Devices corresponding to such reinforced devices were also manufactured from mere thermoplastic matrix polymers by the application of melt working technique.

Table 2 illustrates the matrix polymers and fibrous reinforcements for the devices prepared.

TABLE 2

Structural components for fiber-reinforced biodegradable devices.

| Matrix polymer | Fiber reinforcement |
|---|---|
| PDS | PGA |
| " | PGA/TMC |
| " | PGA/PLLA |
| " | PLLA |
| " | PHBA |
| " | PHBA/HVA |
| " | Chitin fiber |
| " | PDS |
| PDLLA | PGA |
| " | PGA/TMC |
| " | PGA/PLLA |
| " | PLLA |
| " | PHBA |
| " | PHBA/HVA |
| " | PDS |
| " | PDLLA |
| PLLA | PGA |
| " | PGA/TMC |
| " | PLLA |
| PVA | PGA |
| " | PGA/TMC |
| " | PGA/PLLA |
| " | PLLA |
| " | PHBA |
| " | PHBA/HVA |
| " | PDS |
| " | Chitin fibres |
| PGA/TMC | PGA |
| " | PGA/TMC |
| PHBA | PGA |
| " | PGA/TMC |
| " | PHBA |
| Poly-ε-caprolactone | PGA |
| " | PGA/TMC |
| " | PHBA |
| Methylmetacrylate-N-vinylpyrrolidone | PGA |
| Polyurethane | PGA |
| | Collagen (catgut) |
| PEO | PGA |
| " | PGA/TMC |
| " | PGA/PLA |
| " | PLLA |
| n-Butylcyano-acrylate | Collagen (catgut) |
| | PGA |

The devices were secured by their ends to a tension apparatus and were drawn until broken in the direction of longitudinal axis of the device which corresponds to the winding axis of the blank. This was followed by the determination of the relative tensile load-bearing strength (SV) of a reinforced device using the formula: (force required to fracture a reinforced device)/(force required to fracture a corresponding non-reinforced device). The SV values were ranging between 1.5–8.

EXAMPLE 3

Preparation of a self-reinforced polyactide device as shown in FIG. 10 (hereinbelow "helix" (KR)) was formed using a raw material of poly-L-lactide/poly-DL-lactide copolymer (PLLA/PDLLA molar ratio 80/20, Mw 60,000). The helix (KR) was manufactured from a thick, extrusion-made PLLA/PDLLA rod, which was drawn to a drawing ratio of λ=7 at a temperature of 90 degrees for self-reinforcing the material. A thus prepared self-reinforced rod having a thickness of 1 mm was then wound to form "a helix" as described in Example 1. The helix was cut into lengths of 12 mm for the following examination.

Figure 15A:
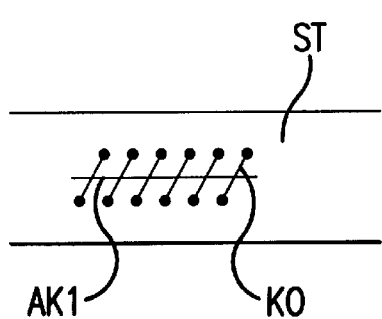
FIG. 15 represents a surgical operation described in Example 3.
Figure 15B:
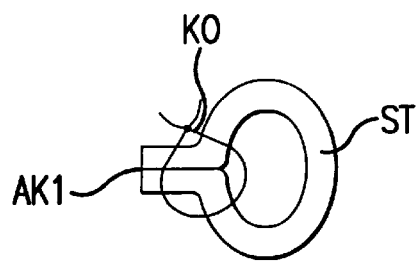

Under general anaesthesia, the gastric cavity of a dog was opened, the intestines were set aside and the bile duct (ST) was exposed by preparation, (see FIG. 15). A roughly 6 mm long incision (AK1) was made in the duct. As shown in FIG. 15a, a distance of 5 mm of this incision was provided with non-resorbable stitches (KO), which pucker up the duct and narrow it permanently together with a cicatricial tissue formed on incision (AK1). This was followed by closing the gastric cavity, stitching the skin and, after waking up from the anaesthesia, the dog was allowed to move freely in its cage.

Figure 15C:
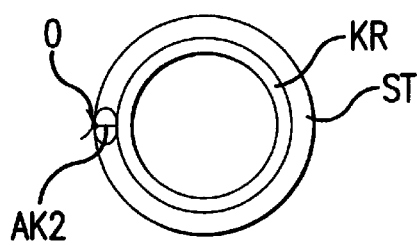
Figure 21:
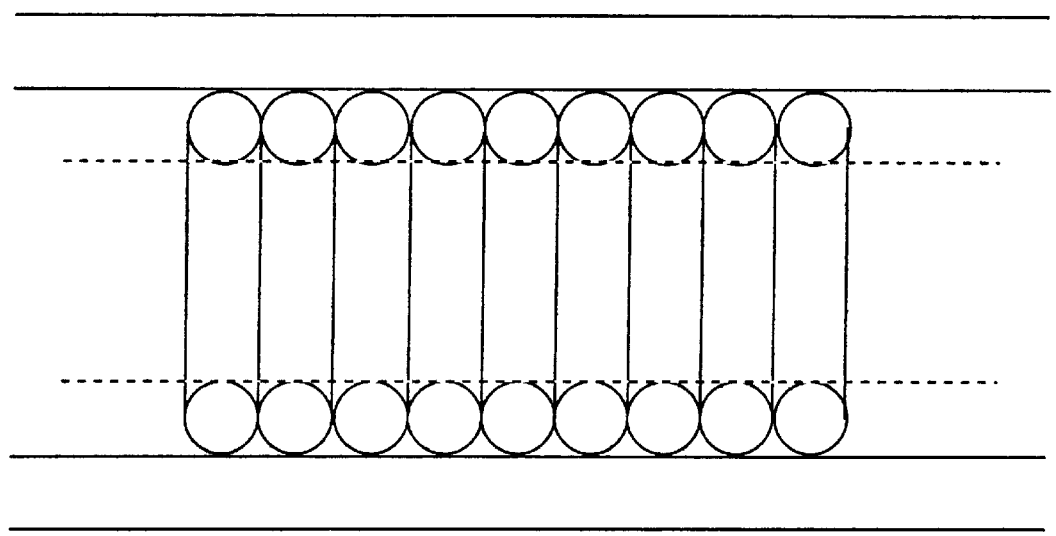
FIG. 21 represents a cross-sectional view of an implant according to an embodiment of the present invention at the time of implanting into a bile duct of a patient.
Figure 22:
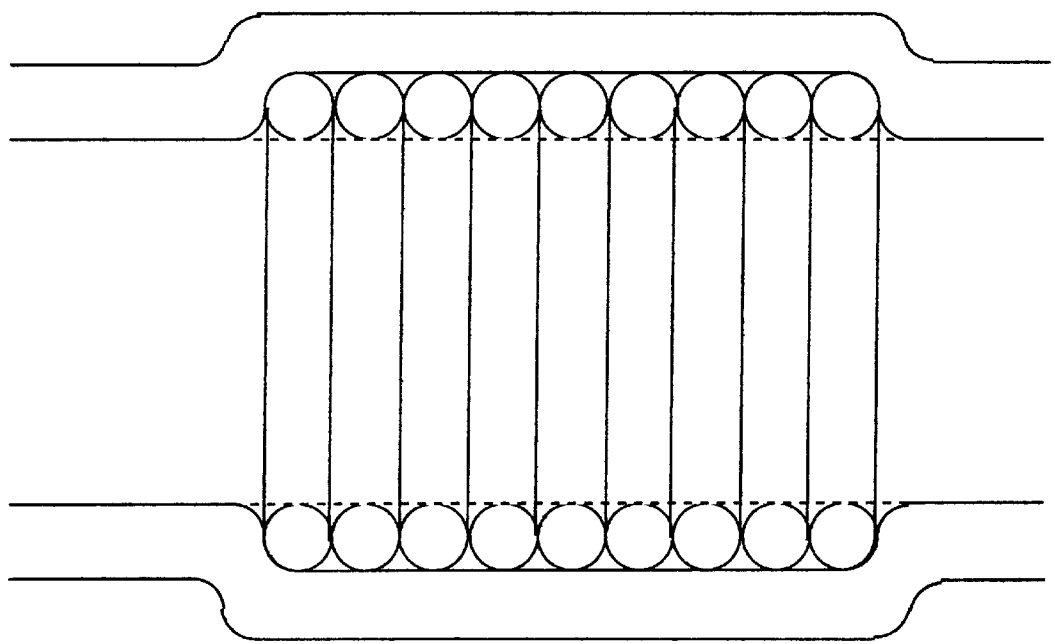
FIG. 22 represents a cross-sectional view of the implant shown in FIG. 21 at some point after implantation, showing the expansion of the device.

After one month, the dog was re-anaesthetized, the gastric cavity was incised and the blocked bile duct was prepared to re-expose it. The duct was opened with a longitudinal incision (AK2) at the region of cicatricial pucker and a helix having an inner diameter of 2 mm and an outer diameter of 3 mm was inserted. The helix was inserted such that both of its ends were located in healthy bile duct and its central portion within the incised pucker region. The bile duct was closed with a stitch (O), whereby its walls extended around the spiral. The situation is schematically illustrated in FIGS. 15c, 21 and 22.

After the operation, the bile duct was normal in volume. In other words, the implant has expanded. Such an expansion of, in this example, the bile duct is a manifestation of the unexpected result that based, at least in part upon the manufacturing technique of the present invention and the reaction of the present invention to body temperatures the present invention is subjected to after an operation, the biodegradable implant of the present invention may expand upon implantation in tissue. This expansion will lock the implant in place. FIGS. 21 and 22 illustrate this aspect of the invention. FIG. 21 represents the implant at the time of implantation and FIG. 22 represents the implant after expansion due to the body conditions has caused the implant to expand. If the implant did not expand, the duct would remain as shown in FIG. 21, with the narrower portion defined by the implant. The gastric cavity and skin were closed the same way as in the first operation. The dog was put away after 14 months by which time the helix had nearly disappeared and the bile duct had a normal extent and volume and the pucker was no longer macroscopically observable.

EXAMPLE 4

Figure 16A:
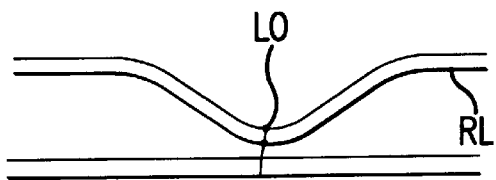
FIG. 16 represents a surgical operation described in Example 4.
Figure 16B:
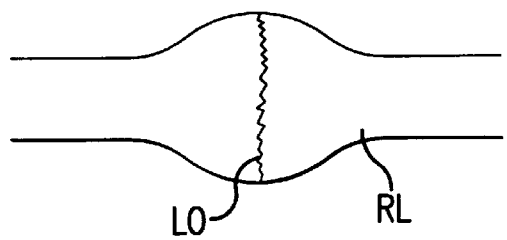
Figure 16C:
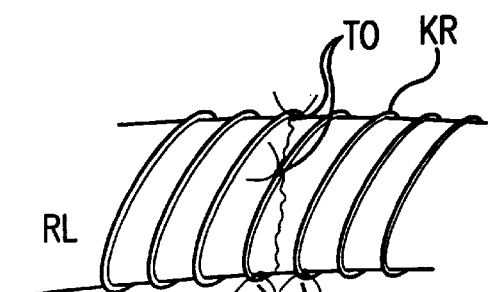

Under general anaesthesia the right hind femoral vein (RL in FIG. 16a) of a dog was cut. The base portion of the more distal vein was threaded into the interior of a biodegradable, reinforced device ("helix") having an inner diameter of 8 mm, an outer diameter of 9 mm and a length of 2 cm. The device, being like the one shown in FIG. 10 (reinforcing fibers: Ca/P-fibers; matrix polymer PLLA, Mw 100,000; fiber/polymer weight ratio=30/70 (w/w) and vein (LO), was stitched with end-to-end technique by using a resorbable 6-0 yarn to make a tight seam with no bleeding. After the operation, due to the flabbiness of the walls, the vein tended to collapse within the region of the stitched seam. This leads to a poorer circulation in the vein resulting easily in the development of a coagulation or clot formed by blood particles within the region of the seam and, thus, the veins will be blocked. The situation is illustrated in the schematic view of FIG. 16a from the side of stitched seam, and in FIG. 16b from above a stitched seam. Therefore, a biodegradable helix (KR) was pulled over the seam portion with the stitched seam remaining at the halfway point of helix (KR). The wall of a vein was attached at the stitched seam over its entire circumference to the helix by means of non-restorable support stitches (TO) (FIG. 16c). This way, the vein was tensioned to its normal extent with the help of a support provided by the device. After the seam had healed, especially after the inner surface of a blood vessel or endothelium had healed, there is no longer a risk of developing a clot and helix can resorb away with no harm done. After 6 months, the dog was put away and the femoral vein had healed with a pucker or clot.

EXAMPLE 5

Figure 17:
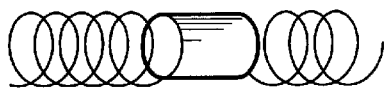
FIG. 17 represents a schematic view of an embodiment of a device according to the present invention described in example 5.

The test animals used in this example were male rabbits weighing 3 kg. The animals were anesthetized for the operation with im. ketamin and iv. pentobarbital preparations. A polylactide blank ($\phi$1 mm) was used to prepare a helix having an outer diameter of 8 mm and a length of 15 mm and an extension formed by a thin tubular neck section, 10 mm, followed by two helical coils (FIG. 17).

The anesthetized test animals were subjected to a surgical incision of the urinary bladder through abdominal covers. Through the opened bladder, the prosthesis was threaded into position with the narrow neck section remaining within the region of closure muscle and the helical coil ends on the side of the urinary bladder.

The prothesis was fitted in 15 test animals which were under observation for 3 months. The study verified that an implant of the invention can be used for preventing a lower urethra obstruction caused by the enlargement of forebland.

EXAMPLE 6

The test animals in this example were male rabbits weighing approximately 3 kg. The animals were anesthetized for the operation with im. ketamin and iv. pentobarbital preparations.

The implants employed were PLLA helixes as described in Example 1 (cross-section of blank circular, thickness of blank 1 mm, outer diameter of helix 6 mm and length 15 mm).

On the anesthetized test animals was performed scission of the blind urethra to the extent sufficient for a prothesis. The prothesis was placed on the distal side of closure muscle. In connection with the operation an antibiotic was administered as a single dose: ampicillin 100 mg/kg.

The prothesis was fitted in 15 animals which were put away with iv overdose of anesthetic 2 weeks, 3 months, 6 months, 1 year and 2 years after the implantation. The urethra was dissected and tissue samples were taken for histological and electron microscopic analysis.

Histological studies indicated that PLLA had caused only slight foreign matter reaction in tissues. Two years after the implantation the helix had nearly completely biodegraded and the urethra was almost normal in its dimensions (i.e. the implant has expanded). This state of the bile duct would not be possible if the bile duct had not expanded at the helix. If the helix had not expanded, there would be a constriction in the duct corresponding to the thickness of the helix wall, as shown in FIG. 21.

EXAMPLE 7

Cloggings in the ureters leading from kidney to bladder will become more common as a result of the increased observation surgery of upper urethras. The ureter has a good regeneration ability when subjected longitudinal incision but its healing requires an internal support. Transverse incision or short deficiency always leads to the development of a clogging.

The purpose of this example was to examine the applicability of a helix made of a biodegradable material both the healing of a longitudinal dissection of the urethra and to the healing of a transverse deficiency.

The test animals were female rabbits weighing approximately 3 kg. The animals were anesthetized. Incision of the abdominal cavity was performed on the flank without opening, however, the actual abdominal cavity.

a) the urethra having a diameter of ca. 4 mm was dissected lengthwise over a distance of ca. 2 cm followed by threading a self-reinforced PGA-helix (blank thickness 1 mm) inside the urethra, the helix having an outer diameter of 4 mm and a length of 20 mm. The region of dissection was covered with fat.

b) a length of ca. 1 cm was cut off the urethra, the remaining ends were dissected over a distance of 0.5 cm and the above-described prothesis was threaded in, so that the remaining defect zone of the tissue was 1 cm. The defect zone was covered with surrounding fat. After 1 month, 3 months and 1 year from the operation a tracer imaging of the kidneys was performed for observing the healing of the urethra. The operated urethras had healed to almost normal condition over the period of 1 year (on the basis of tracer imaging).

In this disclosure, there is shown and described only the preferred embodiments of the invention, but, as aforementioned it is to be understood that the invention is capable of use in various other combinations and environments and is capable of changes or modifications within the scope of the inventive concept as expressed herein.

What is claimed is:

1. A biodegradable surgical device for keeping open a tissue cavity comprising: an elongated blank of biodegradable material which is internally reinforced with biodegradable reinforcement elements oriented in the longitudinal direction of the blank, said blank having a helical configuration comprising a plurality of windings of said blank around a winding center having an axis, wherein said helical configuration is capable of imparting a force in a direction perpendicular to the axis of said winding center.

2. A surgical device according to claim 1, wherein the reinforcement elements comprise at least one element selected from the group consisting of fibers, film fibers, wires, braids, ribbons or staples, non-woven constructions, fabrics or knittings.

3. A surgical device according to claim 1 wherein the helical configuration is generally cylindrical.

4. A surgical device according to claim 1, wherein the reinforcement elements are polymeric.

5. A surgical device according to claim 1, wherein the reenforcement elements comprise at least one element selected from the group consisting of microfibrils and fibrils.

6. A surgical device according to claim 1, wherein the reinforcement elements comprise at least one element selected from the group consisting of fibers, wires, braids, and ribbons.

7. A surgical device according to claim 1, wherein the reinforcement elements comprise biodegradable ceramic fibers.

8. A surgical device according to claim 1, further comprising a second reinforcement element extending between said plurality of windings of said blank.

9. A biodegradable surgical device according to claim 1, wherein the the helical configuration comprises a screw-threaded configuration.

10. A biodegradable surgical device according to claim 1, wherein at least some of the plurality of windings are connected to each other by connecting means.

11. A biodegradable surgical device according to claim 1, wherein the helical configuration comprises a conical configuration.

12. A biodegradable surgical device according to claim 1, further comprising a second elongated blank having a second helical configuration comprising a second plurality of windings of said second blank around a second winding center having a second axis, wherein said second helical configuration is capable of imparting a force in a direction perpendicular to said second axis of said second winding center, wherein said helical configuration and said second helical configuration are at least partially nested within each other.

13. A biodegradable surgical device according to claim 12, wherein the helical configuration and the second helical configuration are twined together to form a substantially tubular structure.

14. A biodegradable surgical device according to claim 10, wherein said connecting means comprise biodegradable radial wires or rods.

* * * * *